(12) United States Patent
Frank et al.

(10) Patent No.: US 10,311,205 B2
(45) Date of Patent: Jun. 4, 2019

(54) ANALYSIS SYSTEM FOR ANALYZING BIOLOGICAL SAMPLES WITH MULTIPLE OPERATING ENVIRONMENTS

(71) Applicant: Roche Molecular Systems, Inc., Pleasanton, CA (US)

(72) Inventors: Paul Frank, Ennetbuergen (CH); Sascha Roehrig, Rotkreuz (CH); Stephan Schweighauser, Rotkreuz (CH)

(73) Assignee: Roche Molecular Systems, Inc., Pleasanton, CA (US)

( * ) Notice: Subject to any disclaimer, the term of this patent is extended or adjusted under 35 U.S.C. 154(b) by 635 days.

(21) Appl. No.: 14/107,668

(22) Filed: Dec. 16, 2013

(65) Prior Publication Data
US 2014/0180601 A1    Jun. 26, 2014

(30) Foreign Application Priority Data

Dec. 21, 2012    (EP) .................................... 12199116

(51) Int. Cl.
| | | |
|---|---|---|
| *G01N 33/48* | (2006.01) | |
| *G06F 19/10* | (2011.01) | |
| *G16H 40/40* | (2018.01) | |
| *G16H 10/40* | (2018.01) | |
| *G06G 7/58* | (2006.01) | |

(52) U.S. Cl.
CPC ............. *G06F 19/10* (2013.01); *G16H 10/40* (2018.01); *G16H 40/40* (2018.01)

(58) Field of Classification Search
None
See application file for complete search history.

(56) References Cited

U.S. PATENT DOCUMENTS 8,201,732 B1    6/2012    Kropf

FOREIGN PATENT DOCUMENTS

WO    2012/174077 A1    12/2012

OTHER PUBLICATIONS

Chen, Haibo, et al., "Live updating operating systems using virtualization," VEE '06, Jun. 14-16, 2006, Ottawa, Ontario, Canada, pp. 35-44.
Crumpler, Stewart, et al., "General Principles of Software Validation; Final Guidance for Industry and FDA Staff," Jan. 11, 2002, Department of Health and Human Services, Food and Drug Administration, Center for Devices and Radiological Health, Center for Biologics Evaluation and Research, 47 pages.
Huber, Ludwig, "Validation of Analytical Methods," Agilent Technologies, Mar. 1, 2010, www.Agilent.com/chem, 76 pages.
McDowall, R. D., "Strategic approaches to laboratory automation," Chemometrics and Intelligent Laboratory Systems: Laboratory Information Management, 1992, vol. 17, pp. 265-282.

*Primary Examiner* — Eric S Dejong

(74) *Attorney, Agent, or Firm* — Kilpatrick Townsend & Stockton LLP

(57) ABSTRACT

An analysis system for biological samples is disclosed that includes at least one analyzer with an analytical unit for analyzing the biological samples and an analyzer controller. The analysis system further includes an analyzer data management system (ADMS) operable for receiving a selection of an operating environment chosen from multiple operating environments. In some embodiments, an analytical system is provided which offers a switch between sample testing and software validation on the same hardware, thereby offering efficiency and flexibility. For example, if sample testing is typically restricted to a particular time of the day (e.g., blood banks often get their samples in the evening and conduct the sample testing at night), the daytime hours can be used to validate new software. In such a case, additional instruments for software validation are not required and expensive idle times of analytical systems are reduced.

16 Claims, 4 Drawing Sheets

ANALYSIS SYSTEM FOR ANALYZING BIOLOGICAL SAMPLES WITH MULTIPLE OPERATING ENVIRONMENTS

CROSS-REFERENCES TO RELATED APPLICATIONS

The present application claims priority from European Patent Application 12199116.0 entitled "Analysis system for analyzing biological samples with multiple operating environments," filed Dec. 21, 2012, the entire contents of which are herein incorporated by reference for all purposes.

FIELD

The invention relates to the automated analysis of biological samples, in particular to systems for controlling multiple implementations of control software.

BACKGROUND

For a reliable diagnosis it is essential that analytical systems obtain accurate and consistent data. When diagnostic or blood screening laboratory acquires a new analytical instrument or installs a new software on existing instruments, they need to perform a validation of analytical system to achieve high-quality standards and to fulfill regulatory requirements. An overview of guidelines and literature can be found in the following documents:
Validation of analytical methods, Ludwig Huber, Agilent Technologies, 2010
Gen. principles of software validation; final guidance for industry and FDA staff, U.S. Department of Health and Human Services, FDA, 2002

Depending on country specific regulations and laboratory standard operating procedures, the validation and verification of analytical systems represent a very expensive and time-consuming procedure. At the moment, diagnostic laboratories need either to buy additional instruments for this process or shutdown analytical testing until the new system is validated.

SUMMARY

The invention provides for an analysis system, a method of validating an analysis system, and a method of operating an analysis system in the independent claims. Embodiments are given in the dependent claims.

Embodiments of the invention may provide for an analytical system which offers a switch between sample testing and software validation on the same hardware. This may have the benefit of significantly reducing costs. For instance if sample testing is temporarily restricted, e.g. usually blood banks get their samples in the evening and conduct the sample test at night, the remaining time can be used to validate a new software. In this case additional instruments for software validation are not required and expensive idle times of analytical systems are reduced.

As will be appreciated by one skilled in the art, aspects of the present invention may be embodied as an apparatus, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer executable code embodied thereon.

Any combination of one or more computer readable medium(s) may be utilized. The computer readable medium may be a computer readable signal medium or a computer readable storage medium. A 'computer-readable storage medium' as used herein encompasses any tangible storage medium which may store instructions which are executable by a processor of a computing device. The computer-readable storage medium may be referred to as a computer-readable non-transitory storage medium. The computer-readable storage medium may also be referred to as a tangible computer readable medium. In some embodiments, a computer-readable storage medium may also be able to store data which is able to be accessed by the processor of the computing device. Examples of computer-readable storage media include, but are not limited to: a floppy disk, a magnetic hard disk drive, a solid state hard disk, flash memory, a USB thumb drive, Random Access Memory (RAM), Read Only Memory (ROM), an optical disk, a magneto-optical disk, and the register file of the processor. Examples of optical disks include Compact Disks (CD) and Digital Versatile Disks (DVD), for example CD-ROM, CD-RW, CD-R, DVD-ROM, DVD-RW, or DVD-R disks. The term computer readable-storage medium also refers to various types of recording media capable of being accessed by the computer device via a network or communication link. For example a data may be retrieved over a modem, over the internet, or over a local area network. Computer executable code embodied on a computer readable medium may be transmitted using any appropriate medium, including but not limited to wireless, wireline, optical fiber cable, RF, etc., or any suitable combination of the foregoing.

A computer readable signal medium may include a propagated data signal with computer executable code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

'Computer memory' or 'memory' is an example of a computer-readable storage medium. Computer memory is any memory which is directly accessible to a processor. 'Computer storage' or 'storage' is a further example of a computer-readable storage medium. Computer storage is any non-volatile computer-readable storage medium. In some embodiments computer storage may also be computer memory or vice versa.

A 'processor' as used herein encompasses an electronic component which is able to execute a program or machine executable instruction or computer executable code. References to the computing device comprising "a processor" should be interpreted as possibly containing more than one processor or processing core. The processor may for instance be a multi-core processor. A processor may also refer to a collection of processors within a single computer system or distributed amongst multiple computer systems. The term computing device should also be interpreted to possibly refer to a collection or network of computing devices each comprising a processor or processors. The computer executable code may be executed by multiple processors that may be within the same computing device or which may even be distributed across multiple computing devices. A 'computing device' or 'computer' as used herein encompasses to any device comprising a processor.

Computer executable code may comprise machine executable instructions or a program which causes a processor to perform an aspect of the present invention. Computer executable code for carrying out operations for aspects of the present invention may be written in any combination of one or more programming languages, including an object oriented programming language such as Java, Smalltalk, C++ or the like and conventional procedural programming languages, such as the "C" programming language or similar programming languages and compiled into machine executable instructions. In some instances the computer executable code may be in the form of a high level language or in a pre-compiled form and be used in conjunction with an interpreter which generates the machine executable instructions on the fly.

The computer executable code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described with reference to flowchart illustrations and/or block diagrams of methods, apparatus (systems) and computer program products according to embodiments of the invention. It will be understood that each block or a portion of the blocks of the flowchart, illustrations, and/or block diagrams, can be implemented by computer program instructions in form of computer executable code when applicable. It is further understood that, when not mutually exclusive, combinations of blocks in different flowcharts, illustrations, and/or block diagrams may be combined. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

A 'user interface' as used herein is an interface which allows a user or operator to interact with a computer or computer system. A 'user interface' may also be referred to as a 'human interface device.' A user interface may provide information or data to the operator and/or receive information or data from the operator. A user interface may enable input from an operator to be received by the computer and may provide output to the user from the computer. In other words, the user interface may allow an operator to control or manipulate a computer and the interface may allow the computer indicate the effects of the operator's control or manipulation. The display of data or information on a display or a graphical user interface is an example of providing information to an operator. The receiving of data through a keyboard, mouse, trackball, touchpad, pointing stick, graphics tablet, joystick, gamepad, webcam, headset, gear sticks, steering wheel, pedals, wired glove, dance pad, remote control, one or more switches, one or more buttons, and accelerometer are all examples of user interface components which enable the receiving of information or data from an operator.

A 'hardware interface' as used herein encompasses a interface which enables the processor of a computer system to interact with and/or control an external computing device and/or apparatus. A hardware interface may allow a processor to send control signals or instructions to an external computing device and/or apparatus. A hardware interface may also enable a processor to exchange data with an external computing device and/or apparatus. Examples of a hardware interface include, but are not limited to: a universal serial bus, IEEE 1394 port, parallel port, IEEE 1284 port, serial port, RS-232 port, IEEE-488 port, Bluetooth connection, Wireless local area network connection, TCP/IP connection, Ethernet connection, control voltage interface, MIDI interface, analog input interface, and digital input interface.

A 'display' or 'display device' as used herein encompasses an output device or a user interface adapted for displaying images or data. A display may output visual, audio, and or tactile data. Examples of a display include, but are not limited to: a computer monitor, a television screen, a touch screen, tactile electronic display, Braille screen, Cathode ray tube (CRT), Storage tube, Bistable display, Electronic paper, Vector display, Flat panel display, Vacuum fluorescent display (VF), Light-emitting diode (LED) displays, Electroluminescent display (ELD), Plasma display panels (PDP), Liquid crystal display (LCD), Organic light-emitting diode displays (OLED), a projector, and Head-mounted display.

A 'database' as used herein encompasses a data file or repository which contains data that may be accessed by a processor. Examples of databases are, but are not limited to: a data file, a relational database, a file system folder containing data files, and a spreadsheet file.

A 'network connection' as used herein encompasses a means for exchanging data between two distinct computers or computing devices. A computing device establishes a network connection using a network interface. Examples of networks include, but are not limited to: Bluetooth network, WIFI network, LAN, and internet protocols.

In one aspect the invention provides for an analysis system for analyzing biological samples. The analysis system comprises at least one analyzer. The analyzer comprises an analytical unit for analyzing a biological sample to obtain an analysis result.

The term 'analytical unit' refers to a device being operable to execute one or multiple analyses on biological samples such as blood, urine, saliva, or other sample types. An analytical unit is operable to determine via various chemical, biological, physical, optical or other technical procedures a parameter of the sample or a component thereof, the parameter in the following being referred to as 'measurement value'. An analytical unit is operable to measure said parameter of the sample or of at least one analyte and return the obtained measurement value. The list of possible analysis results returned by the analyzer comprises, without limitation, concentrations of the analyte in the sample, a digital (yes or no) result indicating the existence of the analyte in the sample (corresponding to a concentration above the detection level), optical parameters, DNA or RNA sequences, data obtained from mass spectroscopy of proteins or metabolites and physical or chemical parameters of various type. The analysis result or results may be qualitative and/or quantitative.

The analyzer may have more than one analytical unit. It is understood that the reference to 'an' analytical unit is not exclusive to one, it may also represent multiple analytical units. By analyzing a biological sample to obtain an analysis result it is understood that 'obtain' may mean measure an analysis result. The analysis result may be or may comprise measurement data. In some embodiments the analysis result comprises measurement data plus Meta data descriptive of the biological sample and/or the measurement conditions. Each analyzer comprises an analyzer controller (AC). The AC may be a computing device comprising a processor and the AC may be operable for controlling the analytical unit or units. The AC may be abbreviated using the acronym AC.

The analysis system further comprises an analyzer data management system. Analyzer data management system may be abbreviated with the acronym ADMS herein. The ADMS is operable for receiving a selection of a selected operating environment chosen from at least two operating environments. The two operating environments are independent of each other. The ADMS is operable for switching the analysis system to the selected operating environment upon receiving the selection. Each of the at least two operating environments provides an AC operating system operable for implementing an analyzer control system (ACS) and an ADMS operating system operable for implementing a laboratory data management system (LDMS). The ACS may be abbreviated with the acronym ACS. The LDMS may be abbreviated with the acronym LDMS. The ACS is operable for controlling the analytical unit to obtain the analysis result. The ACS is operable to provide the analysis result to the LDMS.

The ADMS is used in the laboratory and is used to control one or more analyzers. Very typically it is used to control multiple analyzers. When used in the laboratory software upgrades can be problematic. This is because it may be necessary to thoroughly test all of the software used on the ADMS and also on the analyzer. This may include the software used for the AC and/or any firmware or software used by the analytical unit. Each operating environment provides a separate set of software and/or operating systems for all of the analyzers and the data management system. The analysis system provides a mechanism for quickly changing all of the software on all of the components of the analysis system. This facilitates switching between the different operating environments. For instance an operating environment which contains software which has been qualified may be used during the normal processing of biological samples in the laboratory. When the ADMS receives a selection of a different operating environment the entire system changes its software automatically. This may be used for instance to check the operation of the various software components and then switch back to the original operating environment for running biological samples. The analysis system may provide a means of ensuring that the proper software is used on each component of the analysis system.

In another embodiment the ADMS and the analyzer communicate via a network connection.

In another embodiment the at least one analyzer further comprises one or more embedded systems operable for receiving commands from the AC. For instance the analytical unit may comprise an embedded system which is used to control it to analyze the biological sample. The ACS is operable for sending commands to the embedded system to control the analytical unit to obtain the analysis result. The at least one embedded system further comprises firmware. The ACS is operable for changing the firmware when switching to the selected operating environment. This embodiment may be particularly beneficial because if it is necessary to change the firmware when going between different operating environments it may require time consuming actions on the part of an operator to change the firmware manually. Any functionality for changing firmware automatically reduces the time to switch between the two operating environments.

In another embodiment the ADMS operating system is operable for transferring the analysis results to a laboratory information system. The laboratory information system may be abbreviated herein using the acronym LIS. An LIS as used herein encompasses a database systems, designed to combine study and sample information with acquired data from laboratory instruments in order to reduce administration and speed the production of the final report—McDowall, Chemom. Intell. Lab. Syste., Lab. Inf. Management 17(1992) 265.

The LDMS comprises a validation flag indicating a testing state and a validated state. This may for instance be a variable stored some place in the memory or file system associated with the operating environment. The validation flag is an indicator of whether the software is currently being tested or needs to be validated. The validation flag is operable for disabling the transferring of the analysis result to the LIS in the testing state. For instance if the particular operating environment is not validated it may not be desirable to transfer the analysis result to the LIS. The LDMS comprises a user interface. The LDMS is operable for receiving a flag selection instruction from the user interface. For instance the user interface may involve a keyboard or graphical user interface and the operator simply selects the desired operating environment. The flag selection instruction is descriptive of the testing state or the validated state. The LDMS is operable for setting the validation flag according to the flag selection instruction.

In another embodiment the LIS and the LDMS communicate via a network connection.

In another embodiment the LDMS is implemented in the ADMS operating system of the selected operating environment. It is further operable for detecting a software change in the selected operating environment. The LDMS is operable for setting the validation flag to the testing state if a software change is detected. For instance if any new software is installed on the analyzer, firmware, or elsewhere in the ADMS the LDMS may be operable to automatically change the validation flag from a validated state to a testing state. This may be beneficial because it may prevent unauthorized installation of software onto the analysis system. This may provide higher security to the analysis system and better integrity to the analysis result. For instance if an unauthorized software installation were performed it may compromise the integrity of the data and call the validity of the analysis result into question. This for instance could detect a software change in the operating system of the ADMS or the analyzer.

In another embodiment the ADMS comprises an ADMS boot loader. The ADMS comprises an ADMS storage device. The ADMS storage device comprises an ADMS system storage device partition for each of the at least two operating environments. The ADMS boot loader is operable for receiving the selection. The selection determines a chosen ADMS storage device partition selected from an ADMS storage device partition for each of the at least two operating environments. The ADMS boot loader is operable for booting the ADMS into the chosen ADMS storage device partition upon receiving the selection.

In other words the ADMS may for instance have a mass storage device such as a hard drive with multiple partitions on it. There is a partition corresponding to each of the operating environments. To ensure that only the proper software is installed to change the operating environment each of the partitions is booted into individually. This provides a secure way of ensuring that the proper software is loaded and that there is no mixing of software between the two operating environments. Essentially the selection of a partition selects which operating environment is used.

In another embodiment the ADMS comprises an ADMS virtualization system for providing an ADMS virtual machine for each of the at least two operating environments. The ADMS virtualization system is operable for receiving the selection. The selection determines an enabled ADMS virtual machine. The enabled ADMS virtual machine is selected from the ADMS virtual machine for each of the at least two operating environments. The ADMS virtualization system is operable such that only the enabled ADMS virtual machine is enabled to request the analysis result from the ACS. The ADMS virtualization system is operable such that only the enabled ADMS virtual machine is enabled to receive data from the LDMS.

In other words in this embodiment the ADMS is implemented by having virtual systems. To control which software is able to request the analysis result the active virtual machine is switched and only one virtual machine is able to request the analysis result. This embodiment may have the benefit that more than one of the virtual machines can be used at the same time. For instance various actions may be needed to perform a software validation of a particular operating environment. The operating environment which is used to currently run the laboratory may be used and may control the at least one analyzer. However, in the background the virtual machine which represents the operating environment for a testing version may be performing actions which do not require access to the analyzers at the current time.

In another embodiment the ADMS virtualization system is operable for connecting an unselected virtual machine to an emulator operable for emulating the at least one analyzer. The unselected virtual machine is chosen from the ADMS virtual machine for each of the at least two operating environments. The unselected virtual machine is not the enabled ADMS virtual machine.

In another embodiment the analyzer comprises an AC boot loader. The AC comprises an AC storage device. The AC storage device comprises an AC storage device partition for each of the at least two operating environments. The AC boot loader is operable for receiving the selection from the ADMS. The selection determines a chosen AC storage device partition. The AC boot loader is operable for booting the AC into the chosen AC storage device partition upon receiving the selection. In this embodiment the AC has a storage device with multiple partitions in it. To separate the software the AC is operable to boot into one of the partitions. This may be beneficial because a complete software environment can be implemented using a particular partition and it is secure in separating the various software components in different operating environments from each other. So essentially in this embodiment the selection of the partition selects which operating environment is used.

In another embodiment the AC comprises an analyzer virtual system for providing an analyzer virtual machine for each of the at least two operating environments. The analyzer virtualization system is operable for receiving the selection. The selection determines an enabled analyzer virtual machine. The enabled analyzer virtual machine is selected from the analyzer virtual machine for each of the at least two operating environments. The analyzer virtualization system is operable such that only the enabled analyzer virtual machine is enabled to control the analyzer to analyze the biological sample. The virtualization system is operable such that only the enabled analyzer virtual machine is enabled to send the analysis result to the LDMS of the selected operating environment. In this embodiment there is a virtual machine corresponding to each of the operating environments. The operating environment is selected by enabling one of the virtual machines.

In another embodiment each of the at least two operating systems has a unique identifier. The ADMS is operable for sending the unique identifier to each AC of the at least one analyzer. The AC is operable for switching to the chosen operating system upon receipt of the unique identifier.

In another embodiment each of the at least two operating systems has a unique identifier. The AC is operable for requesting the unique identifier from the ADMS when the AC is turned on. This embodiment may be beneficial because the AC may be turned off when the selection is received. This embodiment ensures that the AC will be operating the proper operating environment.

In another embodiment the at least two operating environments is at least three operating environments. At least one of the at least three operating systems comprises a training environment. A training environment as used herein is an environment used for training an operator how to use the analysis system. The training environment may or may not have access to operate the at least one analyzer. In some embodiments emulators may be used in place of the analyzer.

In another embodiment the LDMS is operable for requesting the analysis result from the ACS. The ACS is operable for controlling the analytical unit to obtain the measurement data. The AC is operable to provide the analysis result to the LDMS. The ADMS is operable to switch to the selected operating environment upon receiving the selection. The AC or ACS may be operable to switch to the selected operating environment upon receiving selection. If there is a training environment the training environment may not be connected to the LIS.

In another aspect the invention provides for a method of validating an analysis system according to an embodiment of the invention. One of the at least two operating environments is an unvalidated operating environment. This may be equivalent to the validation flag being set to the testing state. The method comprises the step of selecting the unvalidated operating environment as the selected operating environment. The method further comprises the step of at least partially performing a validation protocol using the unvalidated operating environment if the unvalidated operating environment is the selected operating environment. The method further comprises the step of validating the unvalidated operating environment if the validation protocol is performed fully and if the validation protocol is successful.

In another aspect the invention provides for a method of operating an analysis system according to an embodiment. One of the at least two operating environments is a validated operating environment. One of the at least two operating environments is an unvalidated operating environment. The validated operating environment may have a validation flag set to the validated state and the unvalidated operating environment may have the validation flag set to the testing state. The method comprises the step of repeatedly selecting the validated operating environment as the selected operating environment. The method further comprises the step of repeatedly acquiring the analysis result using the validated operating environment if the validated operating environment is the selected operating environment. The method further comprises the step of repeatedly selecting the unvalidated operating environment as the selected operating environment. The method further comprises the step of repeatedly at least partially performing a validation protocol using the unvalidated operating environment if the unvalidated operating environment is the selected operating environment. The method further comprises the step of validating the unvalidated operating environment if the validation protocol is performed fully and if the validation protocol is successful. A validation protocol as used herein encompasses as set of testing routines performed using the analysis system to validate that the ADMS and the at least one analyzer are acquiring the proper analysis results.

In another aspect the invention provides for a method of operating an analysis system according to an embodiment of the invention. One of the at least two operating environments is a validated operating environment. This may mean that the validation flag is set to the validated state. The method comprises the step of selecting the validated operating environment as the selected operating environment. The method further comprises the step of acquiring the analysis result using the validated operating environment if the validated operating environment is the selected operating environment. The method further comprises the step of sending the analysis result to the laboratory information system.

It is understood that one or more of the aforementioned embodiments of the invention may be combined as long as the combined embodiments are not mutually exclusive.

BRIEF DESCRIPTION OF THE DRAWINGS

In the following embodiments of the invention are explained in greater detail, by way of example only, making reference to the drawings in which.

DETAILED DESCRIPTION

Like numbered elements in these figures are either equivalent elements or perform the same function. Elements which have been discussed previously will not necessarily be discussed in later figures if the function is equivalent.

Figure 1:
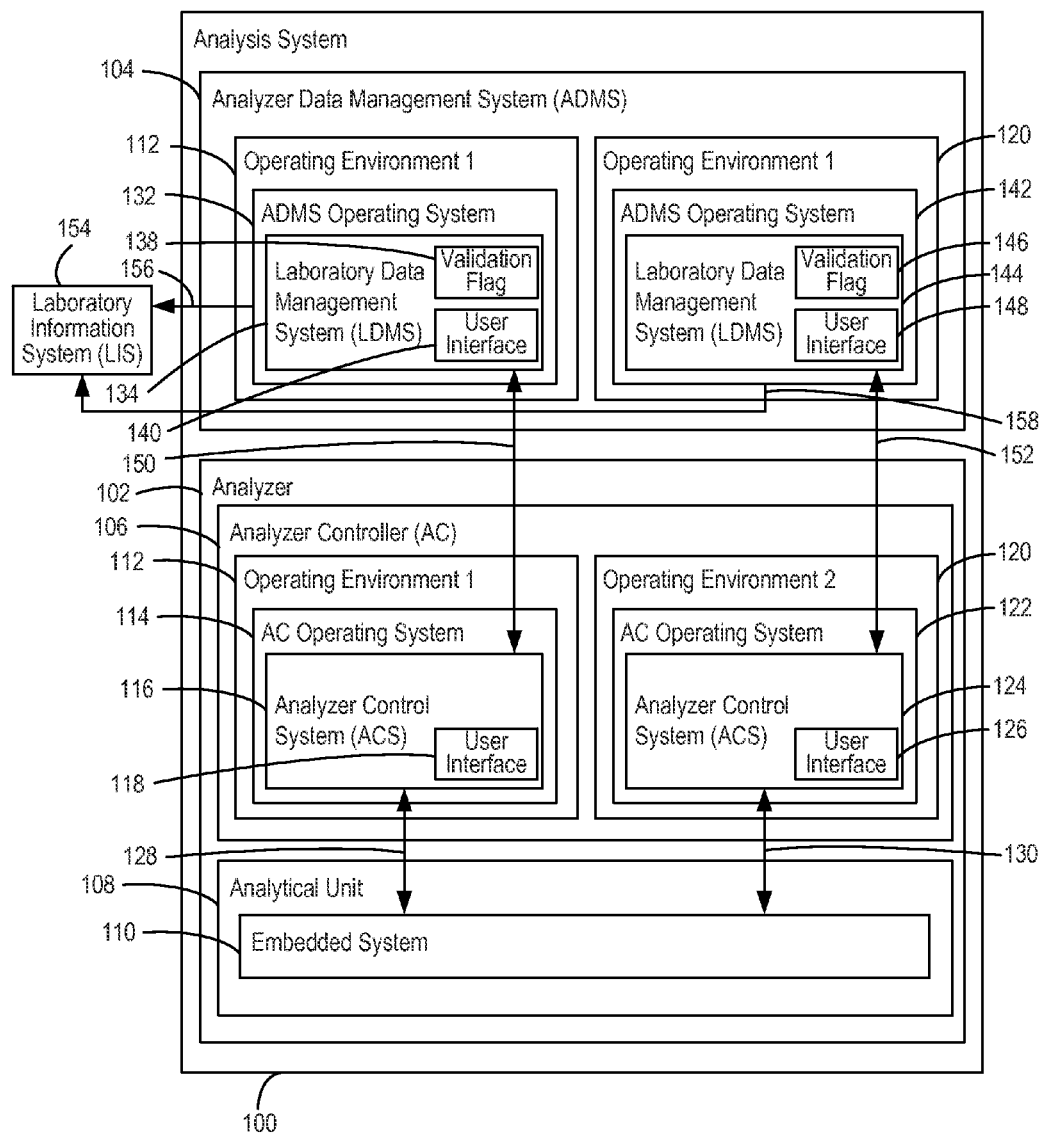
FIG. 1 illustrates a functional diagram of an analysis system according to an embodiment of the invention.

FIG. 1 shows a functional diagram of an analysis system 100 according to an embodiment of the invention. The analysis system 100 comprises an analyzer 102 and an ADMS 104. The analyzer 102 comprises an AC 106 and an analytical unit 108. The analytical unit is operable for analyzing a biological sample to obtain an analysis result. The analytical unit 108 may comprise an embedded system 110 for controlling the analytical unit 108. The AC 106 is operable for supporting multiple operating environments 112, 120. The first operating environment 112 is shown as having an AC operating system 114 which implements an ACS 116. The ACS 116 may have a user interface 118 which enables an operator to control or modify the behavior of the ACS 116. The AC 106 in this example also supports a second operating environment 120.

The second operating environment 120 has an AC operating system 122 which implements an ACS 124. The ACS 124 may also have a user interface 126 for an operator to use. The ACS 116, 124 contains software code which enables the analyzer to control the analytical unit. There is a connection 128 between the ACS 116 and the embedded system 110. There is also shown a connection 130 between the ACS 124 and the embedded system 110.

The ADMS 104 is shown as also supporting operating environment 112 and operating environment 2 120. Only operating environment 1 112 or operating environment 2 120 is active at one time. Both the same operating environment is active in both the ADMS 104 and the AC 106. In the ADMS operating environment 1 has an ADMS operating system 132. Within the ADMS operating system 132 is implemented an LDMS which comprises a validation flag 138 and a user interface 140. The user interface 140 may be used for an operator to control the functioning of the ADMS and also to send a command to the ADMS to switch the operating environment. The validation flag 138 for instance may be used to indicate a testing state or a validated state.

The ADMS 104 is also shown as implementing the operating environment 2 120. As with the first operating environment 142 the second operating environment 120 also implements an ADMS operating system 142 which contains an LDMS 144. The LDMS 144 also comprises a validation flag 146 and a user interface 148. The validation flag 146 may also comprise or be indicative of a testing state or a validated state. The user interface 148 has the same function as user interface 140. The LDMS 134 is shown as having a network connection 150 to the ACS 116.

The LDMS 144 is shown as having a network connection 152 to the ACS 124. Depending upon the state of the validation flag 138 the network connections 150, 152 may be enabled or disabled. In this embodiment the ADMS Operating System 132 is shown as having a network connection 156 to a LIS 154. The LDMS 144 is shown as having a network connection 158 to the LIS 154. In some embodiments the validation flag 138, 146 being set to a testing state may disable the network connection 156 or 158.

In this example only the first operating environment 112 or the second operating environment 120 is active at a particular time. The example shown in FIG. 1 is intended to be representative and may represent systems where the ADMS 104 is implemented using a virtual system or individual partitions. Similarly the AC 106 may implement virtual systems for the operating environments 112, 120 or it may contain separate boot partitions for booting the AC into.

Figure 2:
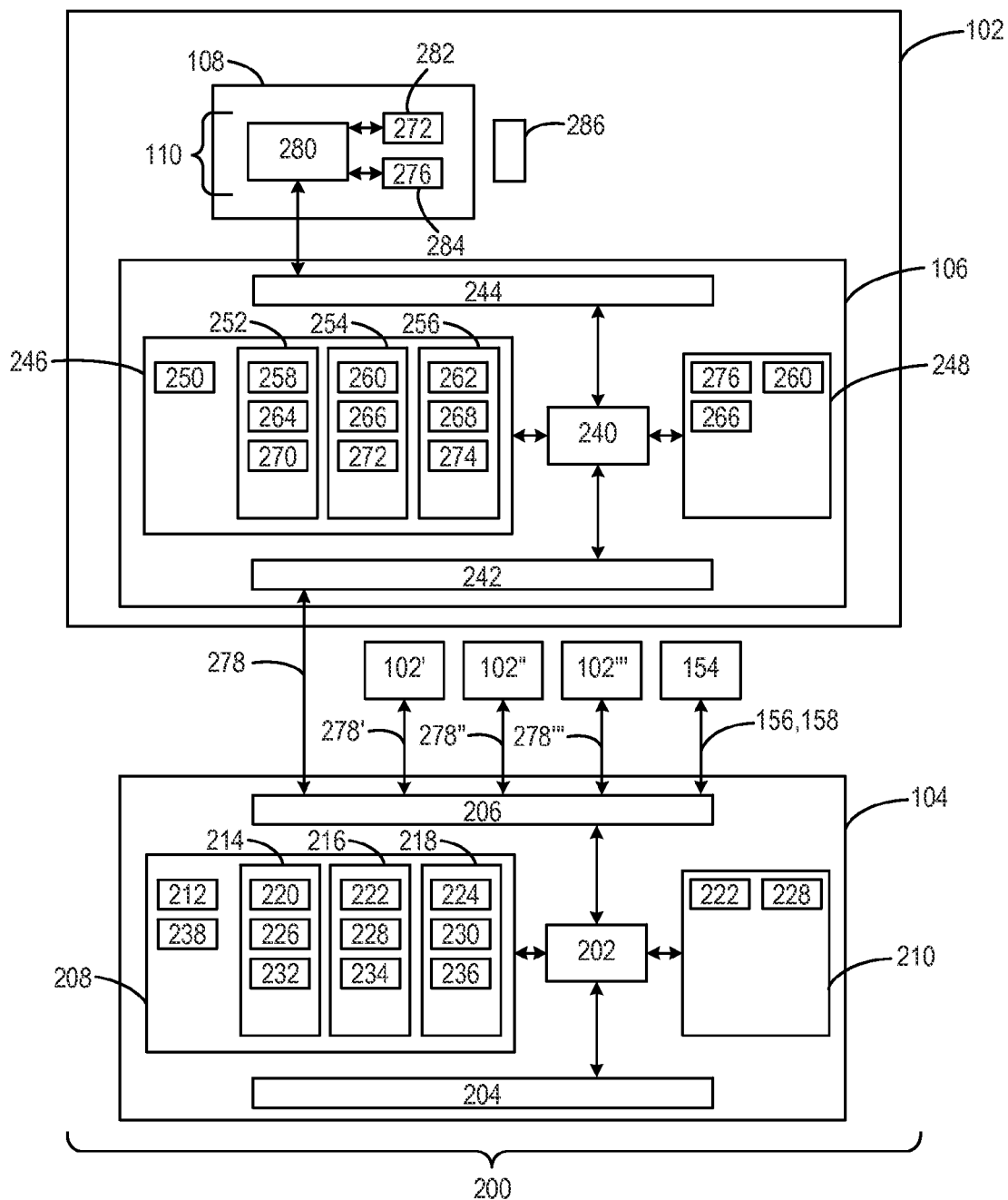
FIG. 2 illustrates a functional diagram of an analysis system according to a further embodiment of the invention.

FIG. 2 illustrates an implementation of an analysis system 200. The analysis system comprises an analyzer 102 and an ADMS 104. The ADMS 104 is shown as comprising a processor 202. The processor 202 is in communication with a user interface 204, a network interface 206, computer storage 208 and computer memory 210.

The computer storage 208 is shown as containing a boot loader 212. The boot loader is operable for loading in this example a first partition 214, a second partition 216, and a third partition 218. There is a first operating system 220 in the first partition 214. There is a second operating system 222 in the second partition 216. There is a third operating system 224 within the third partition 218. There is a first LDMS implementation 226 in the first partition 214. There is a second LDMS implementation 228 in the second partition 216. There is a third LDMS implementation 230 in the third partition 218. There is a first validation flag 232 in the first partition 214. There is a second validation flag 234 in the second partition 216. There is a third validation flag 236 in the third partition 218. The storage 208 is also shown as containing a selection 238 which identifies which partition 214, 216, 218 should be booted into.

The boot loader loads any one of the three partitions 214, 216, 218 when a particular partition is loaded the operating system 220, 222, or 224 selected boots. The operating system then loads a particular LDMS implementation 226, 228, 230. In this way the software can be separated securely. The validation flags 232, 234, 236 are used to select whether the LDMS implementation 226, 228, 230 is in a testing state or a validated state. The validation flag 232, 234, 236 may be used to control the operation of how the LDMS implementation 226, 228, 230 interacts with other components of the analysis system. For instance the LDMS 226, 228, 230 may be prevented from communicating with the LIS 154. Alternatively the data may be transferred to the LIS 154, but the data is flagged as containing invalid results.

The computer memory 210 is shown as having the operating system 222 loaded from partition 216. Accordingly the LDMS implementation 228 also from the second partition 216 is in the memory 210. The memory 210 is also shown as containing a selection 238 of one of the analysis systems. In some embodiments, the boot loader checks the selection at startup and boot into the correct partition. In this case a change in the operating configuration is performed by the LDMS 228. The LDMS changes the selection 238 and the system is rebooted. The change in the selection 238 may cause the LDMS implementation 228 to communicate with the boot loader 212 and instruct the ADMS 104 to reboot into a different partition such as 214 or 218.

The analyzer 102 is shown as also containing AC 106 with a processor 240. The processor 240 is in communication with a network connection 242, a hardware interface 244, computer storage 246, and computer memory 248. The computer storage 246 is shown as containing a boot loader 250 which is operable for booting the ADMS into a first partition 252, a second partition 254, or a third partition 256. There is a first operating system 258 located in a first partition. There is a second operating system 260 located within the second partition 254. There is a third operating system 262 within the third partition 256. There is a first ACS 264 within the first partition 252. There is a second ACS 266 within the second partition 254. There is a third ACS 268 within the third partition 256. There is first firmware 270 within the first partition 254. There is second firmware 272 within the second partition 254. There is a third firmware 274 within the third partition.

The firmware 270, 272, 274 is for the analytical unit 108. The computer memory 248 is shown as containing the second operating system 260 and the second implementation of the ACS 266. The selection 238 can be communicated from the ADMS 104 to the AC 106 in order to cause the boot loader 250 to boot into a particular partition 252, 254, 256. In some embodiments the selection 238 may be stored locally in storage 246 such that the AC 106 automatically boots into the selection partition. In a further embodiment, the AC checks that the locally stored selection matches the selection 238 supplied by the ADMS.

The computer memory 248 is shown as containing an analysis result 276 received from the analytical unit 108. The analysis result 276 may be communicated back to the analyzer 102. A network connection 278 is shown between network interfaces 206 and 242. This enables the ADMS 104 and the analyzer 102 to exchange data and instructions. When a particular operating system is booted into by the AC it may then install the corresponding firmware 270, 272, 274 into the analytical unit 108.

The analytical unit 108 is shown as having an embedded system 110. The embedded system comprises a processor 280 which is in communication with at least two memory locations 282, 284. The first memory location 282 is shown as containing the firmware 272. The firmware 272 may be updated by the corresponding ACS 266. The memory location 284 is shown as containing the measurement result or analysis result 276. 286 represents a biological sample which is measured by the analytical unit 108.

The ADMS 104 may also control additional analyzers 102', 102'', 102''' via network connections 278', 278'', 278'''. The network connection 206 also enables the ADMS 104 to communicate with a LIS 154.

Figure 3:
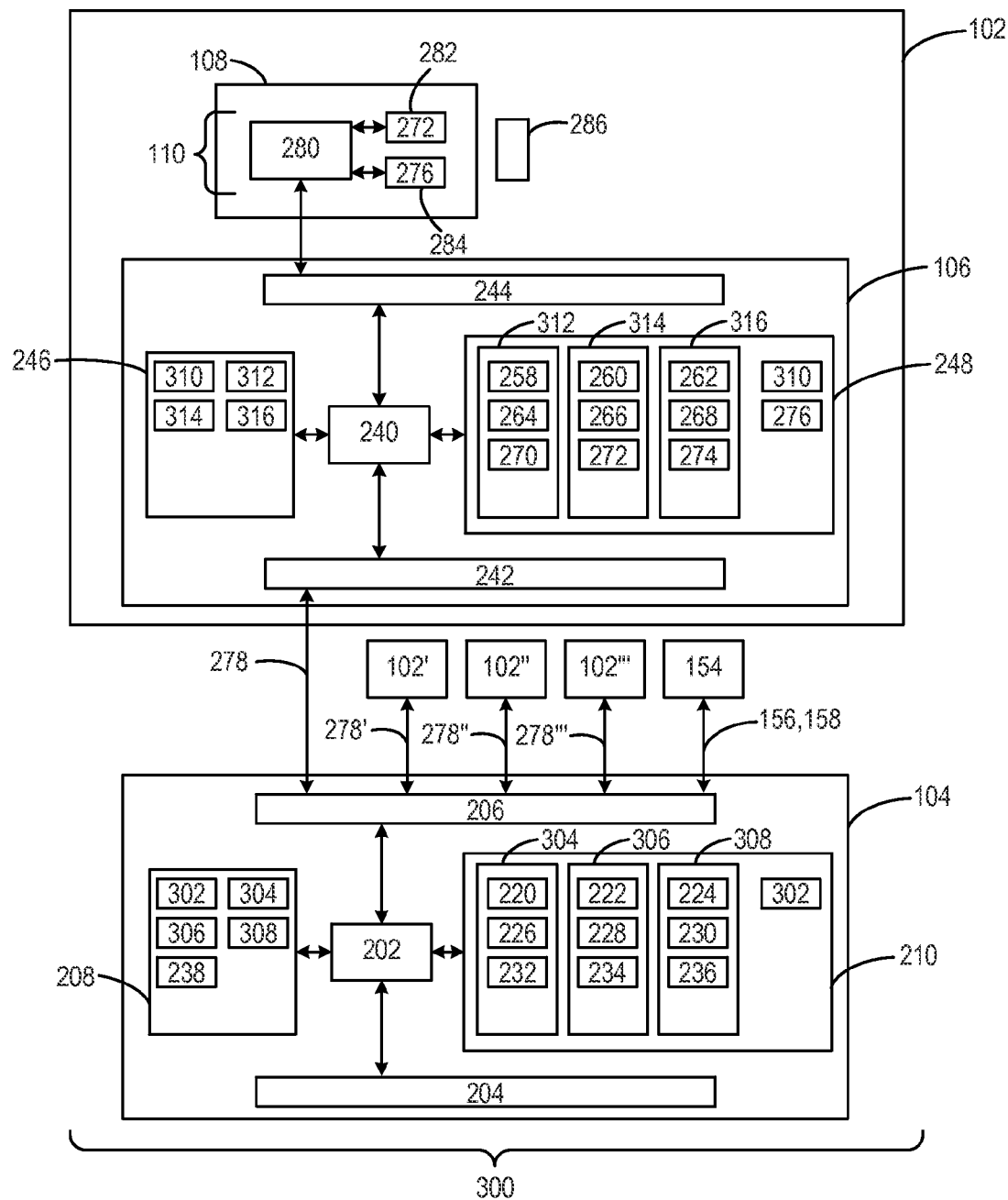
FIG. 3 illustrates a functional diagram of an analysis system according to a further embodiment of the invention.

FIG. 3 shows another embodiment of an analysis system 300 that is similar to that shown in FIG. 2. However, in this example instead of partitions virtual machines are used instead. In the ADMS 104 instead of partitions there is a first virtual machine 304, a second virtual machine 306, and a third virtual machine 308. The virtual machines 304, 306, 308 are shown as using a portion of the storage 208 and the memory 210 of the ADMS 104. There is a host operating system 302 which uses parts of the storage 208 and the memory 210 also. The host operating system 302 contains code which allows a selection 238 received via the user interface 204 to select which of the virtual machines 304, 306 or 308 are active.

The selection 238 is also propagated to the AC 106. The AC 106 is similar to the AC in FIG. 2 except also in this case virtual machines 312, 314, 316 replace the partitions. There is a first virtual machine 312 shown as containing part of the memory consuming part of the storage 246 and memory 248. A second virtual machine 314 also uses a portion of the storage 246 and the memory 248. A third virtual machine 316 also uses a portion of the storage 246 and the memory 248. A host operating system 310 uses a portion of the storage 246 and the memory 248 also. It is operable 310 for controlling which of the virtual machines 312, 314, 316 is active and has control of the analytical unit 108. The choice of the selection 238 is propagated throughout the entire analysis system 300.

In FIG. 2 only partitioning of the storage devices 246, 208 is shown. And in FIG. 3 only the use of virtual machines is used. It should be noted that the use of virtual machines and partitions may be mixed. A network connection 278 is used to connect the ADMS 104 with the analyzer 102 in both cases. The selection 238 can be communicated between the two systems and a choice of using a virtual system or a partitioning of the storage devices may be chosen for each ADMS and/or each analyzer 102. Also in the same system there may be more than one analyzer and one analyzer may use a virtual system and another analyzer may use a partitioning of the storage and boot into different partitions.

Figure 4:
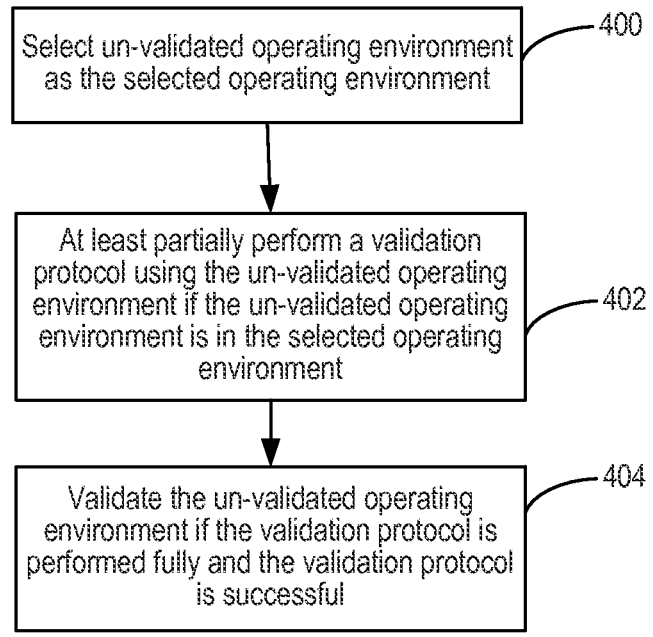
FIG. 4 shows a flow diagram which illustrates a method.

FIG. 4 shows a flow diagram which illustrates a method according to an embodiment of the invention. In this method an analysis system according to an embodiment of the invention is validated. There are at least two operating environments. The method comprises the step of selecting an un-validated operating environment as the selected operating environment. First in step 400 an un-validated operating environment is selected as the selected operating environment. Next in step 402 a validation protocol is at least partially performed using the un-validated operating environment if the un-validated operating environment is in the selected operating environment. Next in step 404 the un-validated operating environment is validated if the validation protocol is performed fully and the validation protocol is successful.

Figure 5:
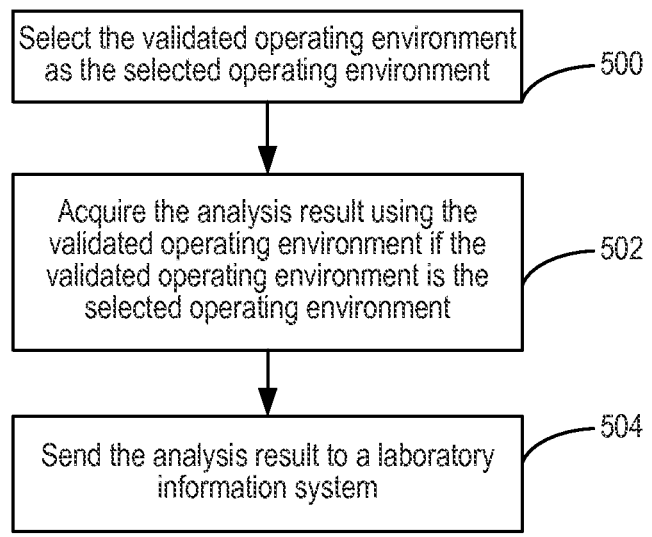
FIG. 5 shows a flow diagram which illustrates a further method.

FIG. 5 shows a flow diagram which illustrates a further method. The flowchart in FIG. 5 illustrates a method of operating an analysis system according to an embodiment of the invention. One of the at least two operating environments is a validated operating environment. In step 500 the validated operating environment is selected as the selected operating environment. In step 502 the analysis result is acquired using the validated operating environment if the validated operating environment is the selected operating environment. Finally in step 504 the analysis result is sent to a laboratory information system.

What is claimed is:

1. An analysis system for analyzing a biological sample in one of at least two operating environments, the analysis system comprising:
at least one analyzer, wherein the at least one analyzer comprises an analytical unit for analyzing the biological sample to obtain an analysis result, wherein each of the at least one analyzer further comprises an analyzer controller (AC) for controlling the analytical unit by loading, into the analytical unit, a corresponding firmware for controlling the analytical unit to analyze the biological sample,
  wherein the AC comprises a first processor, a first memory, and an AC storage device, and wherein the AC storage device comprises an AC storage device partition for each of the at least two operating environments, each AC storage device partition storing an AC operating system for one of the at least two operating environments; and
  wherein the analytical unit comprises a second processor and a second memory; and
an analyzer data management system (ADMS) coupled to the at least one analyzer through a network interface, the ADMS operable for receiving selections of operating environment chosen from the at least two operating environments, wherein the ADMS comprises a third processor, a third memory, and an ADMS storage device, wherein the ADMS storage device comprises an ADMS storage device partition for each of the at least two operating environments, each ADMS storage device partition storing an ADMS operating system for one of the at least two operating environments,
wherein the ADMS is operable for switching the analysis system to one operating environment of the at least two operating environments before and after switching the analysis system to another operating environment of the at least two operating environments upon receiving the selections, by:
  loading a corresponding ADMS operating system from a corresponding ADMS storage device partition into the third memory of the ADMS; and
  sending, through the network interface, an identifier of the one operating environment to the AC to enable a loading of a corresponding AC operating system from a corresponding AC storage device partition into the first memory of the AC;
wherein each AC operating system is operable for implementing an analyzer control system (ACS);
wherein each ADMS operating system is operable for implementing a laboratory data management system (LDMS), the LDMS comprising a validation flag indicating a testing state or a validated state and configured to set the validation flag according to a flag selection instruction or a detection of software change; and
wherein the ACS is operable for loading the corresponding firmware for controlling the analytical unit to analyze the biological sample, and wherein the ACS is operable to provide the analysis result to the LDMS.

2. The analysis system of claim 1, wherein the ADMS operating system is operable for transferring the analysis result to a laboratory information system (LIS), wherein the validation flag is operable for disabling the transferring of the analysis result to the LIS in the testing state, wherein the LDMS comprises a user interface, wherein the LDMS is operable for receiving the flag selection instruction from the user interface, and wherein the flag selection instruction is descriptive of the testing state or the validated state.

3. The analysis system of claim 2, wherein the LDMS implemented in the ADMS operating system of the one operating environment is further operable for detecting a software change in the one operating environment, wherein the LDMS is operable for setting the validation flag to the testing state if the software change is detected.

4. A method of validating an analysis system according claim 1, wherein one of the at least two operating environments is an un-validated operating environment, wherein the method comprises the steps of:
selecting the un-validated operating environment;
at least partially performing a validation protocol using the un-validated operating environment; and
validating the un-validated operating environment if the validation protocol is performed fully and if the validation protocol is successful.

5. A method of operating an analysis system according to claim 1, wherein one of the at least two operating environments is a validated operating environment, wherein the method comprises the steps of:
selecting the validated operating environment;
acquiring the analysis result using the validated operating environment; and
sending the analysis result to a laboratory information system (LIS).

6. The analysis system of claim 1, wherein each AC storage device partition stores a firmware for the analytical unit in a corresponding operating environment, the firmware for the analytical unit, when loaded into a memory of the analytical unit and executed by the analytical unit, causing the analytical unit to analyze the biological sample.

7. A method of operating an analysis system having two or more operating environments, the method comprising:
(a) receiving, by an analyzer data management system (ADMS) of the analysis system from a user through a user interface, a first selection of a first operating environment from the two or more operating environments, the first operating environment including a first ADMS operating system and a first analyzer controller (AC) operating system;

(b) loading, by an ADMS boot loader of the ADMS, the first ADMS operating system from a first ADMS storage device partition into a memory of the ADMS to boot the ADMS into the first operating environment;

(c) sending, by the ADMS to an analyzer controller (AC) of an analyzer of the analysis system, a first identifier of the first operating environment;

(d) loading, by an AC boot loader of the AC based on the first identifier, the first AC operating system from a first AC storage device partition into a memory of the AC to boot the AC into the first operating environment;

(e) performing, by an analysis unit of the analyzer using a first firmware, a first protocol in the first operating environment, the first protocol including a set of test routines;

(f) sending, by the AC to the ADMS, a result of the first protocol;

(g) receiving, by the ADMS through the user interface, a second selection of a second operating environment from the two or more operating environments, the second selection being received before the first protocol is complete, and the second operating environment including a second ADMS operating system and a second AC operating system;

(h) loading, by the ADMS boot loader, the second ADMS operating system from a second ADMS storage device partition into the memory of the ADMS to boot the ADMS into the second operating environment;

(i) sending, by the ADMS to the analyzer controller (AC) of the analyzer, a second identifier of the second operating environment;

(j) loading, by the AC boot loader based on the second identifier, the second AC operating system from a second AC storage device partition into the memory of the AC to boot the AC into the second operating environment;

(k) performing, by the analysis unit of the analyzer using a second firmware, a sample analysis in the second operating environment;

(l) sending, by the AC to the ADMS, a result of the sample analysis;

(m) sending, by the ADMS, the result of the sample analysis to a database; and (n) receiving, by the ADMS through the user interface, a third selection of switching the analysis system back to the first operating environment to continue with the first protocol.

8. The method of claim 7, further comprising:
receiving, by the ADMS through the user interface, a fourth selection of switching the analysis system to a third operating environment.

9. The method of claim 7, further comprising:
setting, by the ADMS, a flag for the first operating environment based on the result of the first protocol, the flag indicating that the first operating environment is in a testing state or a validated state.

10. The method of claim 7, wherein each of the first AC operating system and the second AC operating system is configured to implement an analyzer control system (ACS), the ACS configured to control an analysis unit of the analyzer to perform the first protocol or the sample analysis.

11. The method of claim 7, wherein each of the first ADMS operating system and the second ADMS operating system is configured to implement a laboratory data management system (LDMS), the LDMS configured to set a status of an operating environment based on a user input or the result of a validation protocol.

12. The method of claim 11, wherein the LDMS is further configured to determine whether or not to send a result of a sample analysis to the database based on the status of the operating environment in which the sample analysis is performed.

13. The method of claim 11, wherein the LDMS is further configured to detect a software change in an operating environment and set the status of the operating environment to un-validated if the software change is detected.

14. The method of claim 7, wherein the ADMS is communicatively connected to two or more analyzers for controlling the two or more analyzers.

15. The method of claim 7, further comprising:
requesting, by the ADMS, the result of the first protocol or the result of the sample analysis from the analyzer.

16. The method of claim 7, wherein the first protocol is a validation protocol for validating the first operating environment.

* * * * *